United States Patent
Jimenez-Rios et al.

(10) Patent No.: US 9,358,541 B2
(45) Date of Patent: Jun. 7, 2016

(54) CRYOCANE WITH RACKING CAPABILITY

(71) Applicant: Cook Medical Technologies LLC, Bloomington, IN (US)

(72) Inventors: Jorge L. Jimenez-Rios, Bloomington, IN (US); Bryan Woodard, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 139 days.

(21) Appl. No.: 14/200,488

(22) Filed: Mar. 7, 2014

(65) Prior Publication Data

US 2014/0263115 A1 Sep. 18, 2014

Related U.S. Application Data

(60) Provisional application No. 61/783,454, filed on Mar. 14, 2013.

(51) Int. Cl.
*B65D 25/00* (2006.01)
*B01L 9/06* (2006.01)
*A01N 1/02* (2006.01)
*B01L 7/00* (2006.01)

(52) U.S. Cl.
CPC .................. *B01L 9/06* (2013.01); *A01N 1/0268* (2013.01); *B01L 7/50* (2013.01); *B01L 2300/0861* (2013.01)

(58) Field of Classification Search
CPC ....... B01L 9/06; B01L 2300/086; B01L 7/50; B01L 2300/0861; A01N 1/0268
USPC ............ 220/560.1, 560.04, 560.11, 737, 751, 220/23.83; 62/51.1, 371; 211/74, 71.01; 422/562
See application file for complete search history.

(56) References Cited

U.S. PATENT DOCUMENTS

| | | | |
|---|---|---|---|
| 3,130,836 A | * | 4/1964 | Conrad .................. F25D 25/00 206/499 |
| 3,800,970 A | | 4/1974 | Jackson |
| 4,041,722 A | | 8/1977 | Terlesky et al. |
| 4,306,676 A | | 12/1981 | Edwards et al. |
| 4,363,245 A | | 12/1982 | Schmid |
| 4,365,576 A | | 12/1982 | Cook |
| 4,969,336 A | | 11/1990 | Knippscheer et al. |
| 5,176,002 A | | 1/1993 | O'Brien et al. |
| 5,325,980 A | * | 7/1994 | Grimm ............... B01L 3/50825 215/213 |
| 5,524,774 A | | 6/1996 | Cullen |
| 5,595,395 A | * | 1/1997 | Wilson ..................... B62B 1/14 280/47.19 |

(Continued)

OTHER PUBLICATIONS

International Search Report and Written Opinion for PCT/US2014/020224, dated May 27, 2014, 12 pages.

(Continued)

*Primary Examiner* — Fenn Mathew
*Assistant Examiner* — Don M Anderson
(74) *Attorney, Agent, or Firm* — Brinks Gilson & Lione (57) ABSTRACT

A kit for performing long term storage of biological matter is provided. The kit includes an elongate rod, extending between opposed first and second ends, and at least one holding point disposed upon the rod between the first and second ends, the holding point comprising a recess defined within a wall. A cryovial with an internal volume is configured to receive a biological sample therein, the cryovial comprising at least one finger that extends radially outward from an outer circumference thereof, wherein the finger is configured to releasably mate with the at least one holding point upon the rod.

10 Claims, 8 Drawing Sheets

(56) References Cited

U.S. PATENT DOCUMENTS

| | | |
|---|---|---|
| 6,530,485 B1 | 3/2003 | Weber |
| 6,571,968 B1 | 6/2003 | Cullen |
| 7,311,212 B2 | 12/2007 | Martin et al. |
| 7,445,127 B2 | 11/2008 | Pittman |
| 2002/0083717 A1 | 7/2002 | Mullens et al. |
| 2011/0239791 A1 | 10/2011 | Fici |
| 2011/0259892 A1 | 10/2011 | Cognard et al. |
| 2012/0247999 A1 | 10/2012 | Nishio et al. |
| 2012/0325821 A1 | 12/2012 | Mookerjee |

OTHER PUBLICATIONS

VWR Order Code Index, BNSDOCID: ,XP __55118371A __|_>, 8 pages.

VWR International All You Need for BioBanking, Sample Storage, Sample Handling, Safety, BNSDOCII):<XP__55118371A __|_>, 84 pages.

International Preliminary Report on Patentability and Written Opinion for PCT/US2014/020224, dated Sep. 15, 2015, 6 pp.

* cited by examiner

FIG. 11 even with the edge of the wall 20, 22 such that the neck 32 is open along one edge of the wall 20, 22. In other embodiments, the neck 32 may extend a distance into the wall 20, 22 such that a gap is between an opening to the neck 32 and the edge of the wall 20, 22.

CRYOCANE WITH RACKING CAPABILITY

CROSS-REFERENCE TO RELATED APPLICATIONS

This application claims priority from U.S. provisional application No. 61/783,454 filed on Mar. 14, 2013, the entirety of which is hereby fully incorporated by reference herein.

TECHNICAL FIELD

This disclosure relates to devices to retain multiple containers or vials for long term storage of biological material, such as in a dewar.

BRIEF SUMMARY

A first representative embodiment of the disclosure is provided. The embodiment includes a device for manipulating a plurality of cryovials. The device includes an elongate rod extending between opposed first and second ends, and at least one holding point disposed upon the rod between the first and second ends. The holding point comprising a recess defined within a wall of the rod configured to accept a projection that extends from a cryovial associated with the rod.

Another representative embodiment of the disclosure is provided. The embodiment includes a kit for performing long term storage of biological matter. The kit includes an elongate rod, extending between opposed first and second ends, and at least one holding point disposed upon the rod between the first and second ends, the holding point comprising a recess defined within a wall. A cryovial with an internal volume is configured to receive a biological sample therein, the cryovial comprising at least one finger that extends radially outward from an outer circumference thereof, wherein the finger is configured to releasably mate with the at least one holding point upon the rod.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Turning now to FIGS. 1-6, a device for manipulating and pivotably supporting a plurality of cryovials 100 is provided. The device 10 may be an elongate cryocane, formed as a rod 10. The rod may be formed from opposed and parallel first and second walls 20, 22 that are mutually supported by a base 24. The first and second walls 20, 22 may be arranged and separated from each other at a distance that is just larger than a largest diameter (not including a diameter of the radial fingers 112 (discussed below) of a cryovial 100 that is configured for use with the rod 10), such that the cryovials 100 that are supported by the rod 10 fit between the first and second walls 20, 22 when the rod 10 is in a vertical configuration for placement within a dewar 300 (FIG. 7). In some embodiments, the first and second walls 20, 22 may be planar, or flat, while in other embodiments, the first and second walls 20, 22 may be arcuate along all or a portion of their cross-section. In still other embodiments, the first and second walls may have a "C" shaped cross-section, or a "U" shaped cross-section.

The rod 10 includes one or a plurality of holding points 30 that are configured to receive and support a finger 112 that extends radially outward from a cryovial 100. The holding point 30 may be a recess that extends from a top edge of the respective wall 20, 22 and downward (in the orientation shown in FIG. 1) through the wall. The holding point 30 may be formed in one of a number of types of geometries that will support the finger 112 and allow the finger 112 and therefore the cryovial 100 relative pivoting motion with respect to the rod 10. In some embodiments, a single holding point 30 may be disposed upon the rod 10 to support the cryocane 100, with a single finger 112, while in other embodiments, the first and second walls 20, 22 may each have holding points 30 that are aligned to simultaneously receive fingers 112 that radially extend from opposite sides of a cryocane 100.

Figure 6:
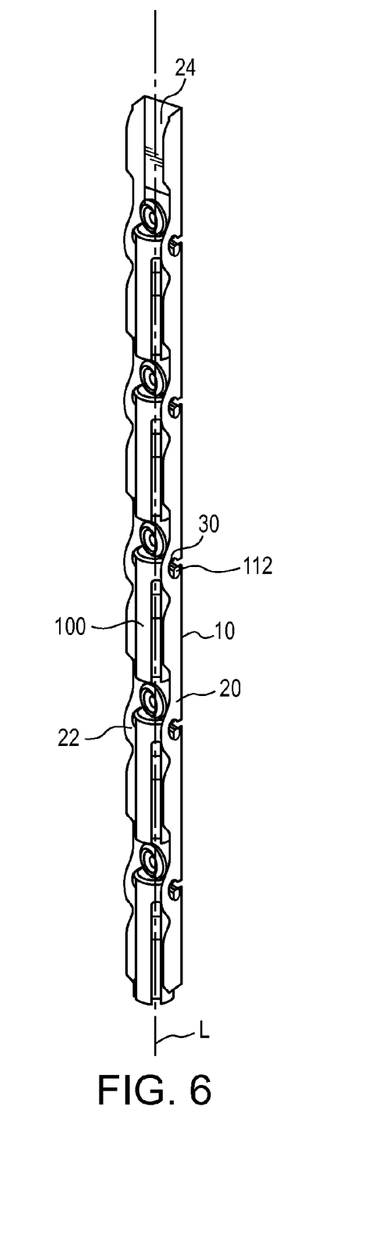
FIG. 6 is a schematic view of the cryocane of FIG. 1 supported vertically and supporting a plurality of cryovials.
Figure 7:
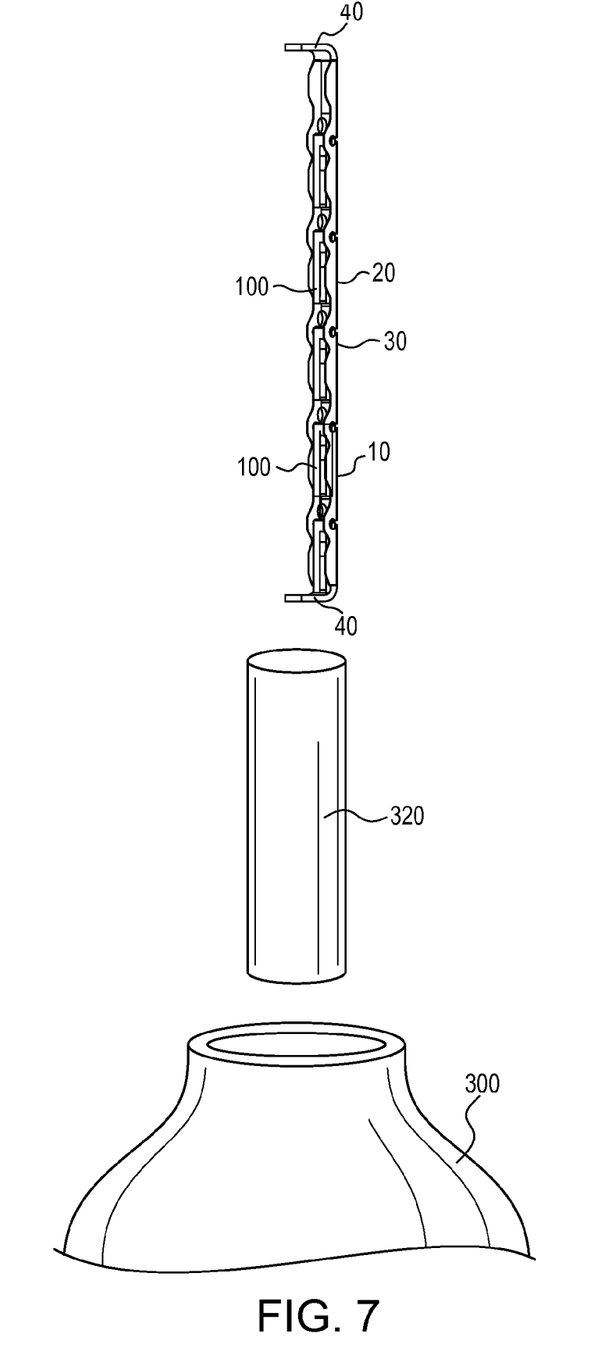
FIG. 7 is a schematic view of the cryocane of FIG. 1 supporting a plurality of cryovials aligned to be positioned within a dewar.

As shown in FIG. 6, in embodiments where the rod 10 (and/or each wall 20, 22 of the rod 10) has a plurality of holding points 30 disposed thereon, the holding points 30 are disposed upon the rod 10 with sufficient space between neighboring holding points to allow the cryovials 100 disposed upon the rod to each be aligned in parallel with the rod 10 when the rod 10 is in the vertical orientation. In other words, the holding points 30 are spaced apart from neighboring holding points 30 a distance greater than the height of the cryovial (including any cap or stopper 120 associated with the cryovial 100).

Figure 3:
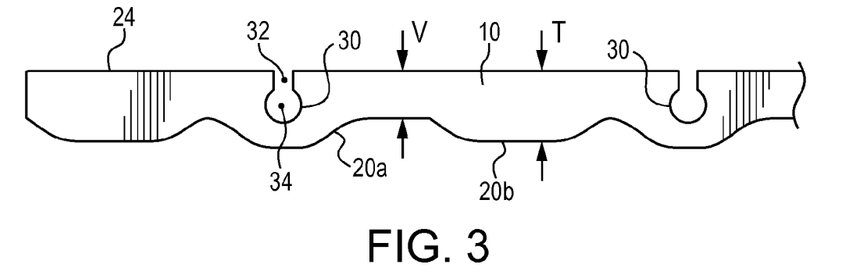
FIG. 3 is a side view of the cryocane of FIG. 1.

For example, as best shown in FIG. 3, the holding point 30 may be a recess that includes a neck 32 that extends below the edge and communicates with an inner cavity 34 that is larger than the neck 32. In some embodiments, the neck 32 may be formed with a width that is larger than a width (i.e. small dimension X of a rectangular finger 112, FIG. 4) but the width is smaller than a height (i.e. the larger diameter Y of the rectangular finger 112, FIG. 4). In this embodiment, the finger 112 is configured to extend from the cryovial 100 in the orientation shown in FIG. 4, such that the finger 112 can slide through the neck 32 when the rod 10 is in a horizontal configuration (FIGS. 4, 5), but is prevented from sliding through neck 32 when the rod 10 is in a vertical configuration (FIGS. 6, 6A).

Figure 4:
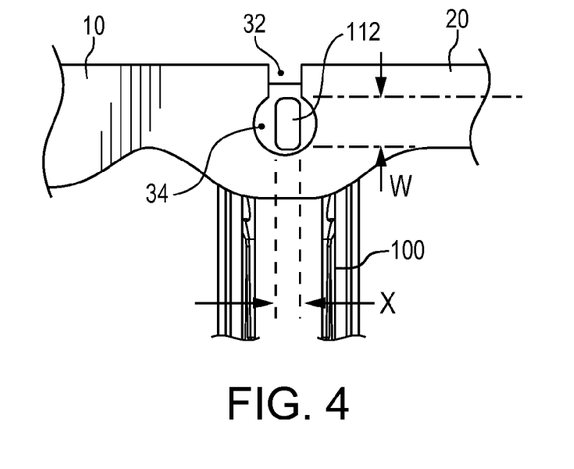
FIG. 4 is a detail view of the finger of a cryovial disposed within a holding point of the cryocane of FIG. 1, with the cryocane disposed in the horizontal configuration.

The inner cavity 34 may be of a circular cross-section as best shown in FIG. 4, with the space formed within the inner cavity 34 communicating with the inner space formed within the neck 32, such that the finger 112 that slides downwardly through the neck 32 ultimately reaches the inner cavity 34. In some embodiments, the neck 32 may be formed with a constant width along its length, while in other embodiments, the neck 32 may be formed as a wedge, with different diameters along its length. The inner cavity 34 may be formed with a diameter along the entire inner cavity 34, or a portion of the circumference of the inner cavity 34 that is larger than the height Y of the finger 112. In embodiments where the inner cavity 34 is not circular, or even arcuate, the dimensions and the orientation of the walls defining the inner cavity 34 may be sized such that the finger 112 fits within the inner cavity 34 and allows for the position of the cryovial 100 to pivot with respect to the rod 10, based upon the finger 112 pivoting within the inner cavity 34. Similarly, in embodiments where the inner cavity 34 is circular or arcuate, the diameter of the inner cavity 34 that is larger than the height Y of the finger 112 allows the finger 112, and therefore the cryovial, to freely pivot with respect to the rod 10.

Figure 8:
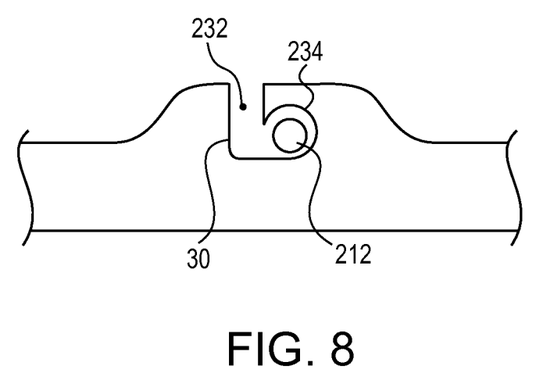
FIG. 8 is a side view of an alternate holding point of a cryocane.
Figure 8A:
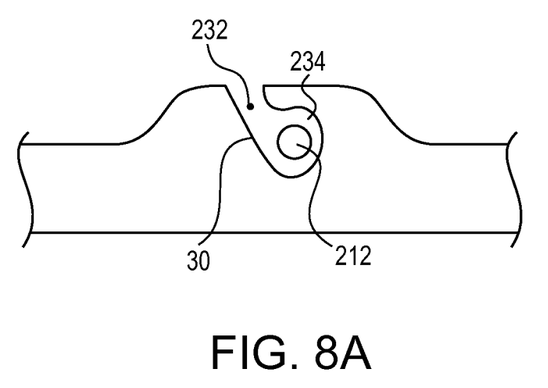
FIG. 8a is a side view of another alternate holding point of a cryocane.

In other embodiments, the holding point 30 may be shaped differently, but preferably with a shape that prevents the finger 112 from escaping the holding point 30 when the rod 10 is both a vertical and a horizontal orientation. For example, with reference to FIG. 8, the holding point 30 may include an elongate neck 232 that connects with an inner cavity 234 that is positioned to a side (either the right or the left) of the neck 232. The neck 232 may be of a width that is just larger than a width X of the finger, but smaller than a height W of the finger 112 (i.e. when the finger has a rectangular cross-section as shown in FIG. 4) to prevent the finger from extending through the neck 232 when the cryovial 100 is aligned with the projection of the height facing the neck 232. In other embodiments, an alternate finger 212 (FIG. 8) may be provided with a round cross-section. The width of the neck 232 may be larger than the diameter of the finger 212 to allow the finger 212 to slide through the neck 232, while the inner cavity 234 is aligned to the side of the neck 232, and preferably the side of the neck 232 that is below the neck 232 when the rod 10 is in the vertical orientation, such that the finger 232 is retained within the holding point 30 when the rod 10 is in both the horizontal and vertical orientations. In some embodiments shown in FIG. 8, the neck 232 may be perpendicular to the surface defining the opening into the neck 232 (or the base 24), while in other embodiments shown in FIG. 8a, the neck 232 may be disposed at an incline or an acute angle with respect to the opening or the base 24. The inclined neck may be beneficial to urge the finger 212 into the inner cavity 234 as the finger 212 slides long the neck 232.

Figure 9:
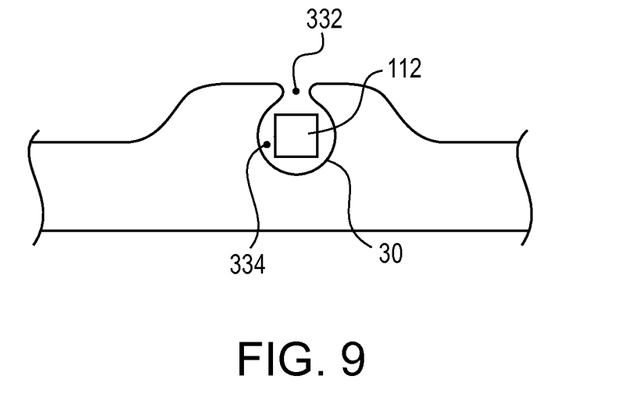
FIG. 9 is a side view of another alternate holding point of a cryocane.

In still other embodiments, the holding point 30 may be formed with a neck 332 and an inner cavity 334, with the inner cavity 334 being just larger than the largest dimension of the finger 112 (212) so that the cryocane 100 can freely pivot with respect to the rod 10 when the finger 112 is within the inner cavity 334. The neck 332 may include a width (either a constant width or a smallest width along the length of the neck 332) that is smaller than the smallest dimension of the finger 332. In this embodiment, at least a portion of the structure that forms the neck may be flexible, such as made from rubber or flexible plastic, to be biased to the normal orientation of the neck 332, but can be temporarily displaced by the finger 112 as it is urged through the neck 332. In other embodiments, the walls 20, 22 forming the neck may be thin enough such that they temporarily deflect to allow the finger 112 to pass therethrough. This embodiment supports the finger 112 within the holding point 30 in both the vertical orientation, while allowing the finger 112 to be inserted into or withdrawn from the holding point 30.

Figure 5:
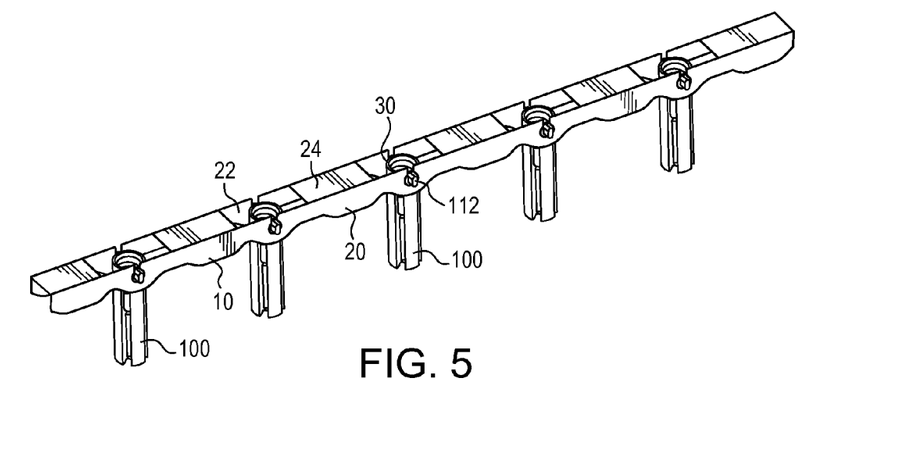
FIG. 5 is a side view of the cryocane of FIG. 1 mounted horizontally and supporting a plurality of cryovials.
Figure 5A:
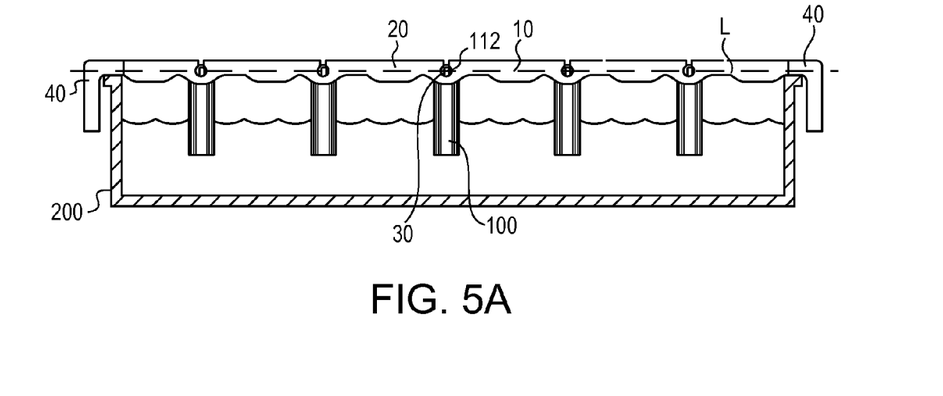
FIG. 5a is a schematic view of the cryocane of FIG. 5 supported horizontally across a bowl and supporting a plurality of cryovials.
Figure 6A:
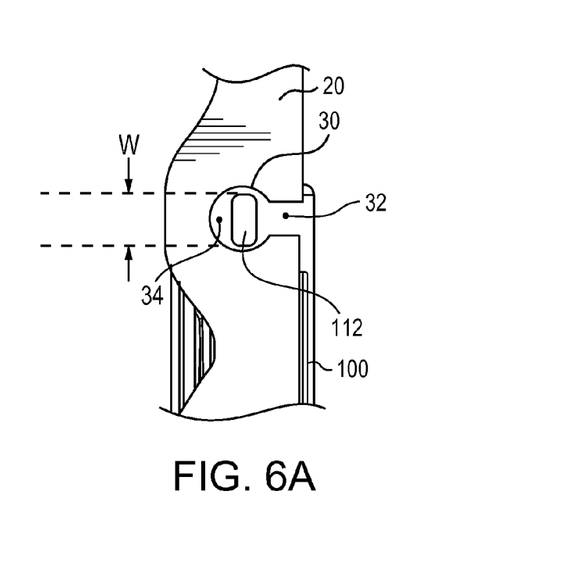
FIG. 6a is a detail view of detail A of FIG. 6.

As will be understood with reference to FIGS. 5 and 6, the engagement between the finger 112 and the inner cavity 34 of the holding point 30 allows the cryovial 100 to pivot with respect to the rod 10. In some operations, the rod 10 may be supported by a user or a support structure (such as a dewar 300 (FIG. 7) or a vitrification bowl 200 (FIG. 5)) and the cryovials 100 are free to pivot with respect to the rod 10. In this situation, the cryovials will normally self-align in steady state vertically due to the force of gravity acting upon the cryovial 100. This vertical alignment will be maintained (in steady state) as the rod 10 is transferred from a horizontal configuration for filling or removing biological matter from within the cryovial 100, to a vertical configuration for placement within the dewar 300. The engagement between the finger 112 and the inner cavity 34 allows the finger 112 to pivot therewithin as the rod 10 pivots to maintain this vertical alignment.

As will be appreciated, the configuration of the neck 32 aids in the functionality of the rod 10 to retain the one or more cryovials 100 pivotably fixed to the rod 10. As shown in FIG. 4, when the rod 10 is in a horizontal configuration, the finger 112 may be aligned within the inner cavity 34 such that the projection of the finger 112 (which includes the width X of the finger 112) that is aligned with the neck 32 is smaller than the cross-sectional area of the neck 32, but the downward forces of gravity retain the fingers 112 within the inner cavity 34, even when the cryovial 100 is pivoted with respect to a horizontal rod 10. In contrast, as best shown in FIG. 6A, when the rod 10 is in a vertical orientation the projection of the finger 112 (which includes the height W of the finger 112) is larger than the cross-sectional area of the neck 32, which prevents the finger 112 from sliding through the neck in that configuration. The cryovials 100 supported upon the rod 10 are urged to a vertical orientation (in parallel with the rod 10) in this orientation, so the fingers 112 cannot slide out of the neck 32 in this configuration.

Figure 1:
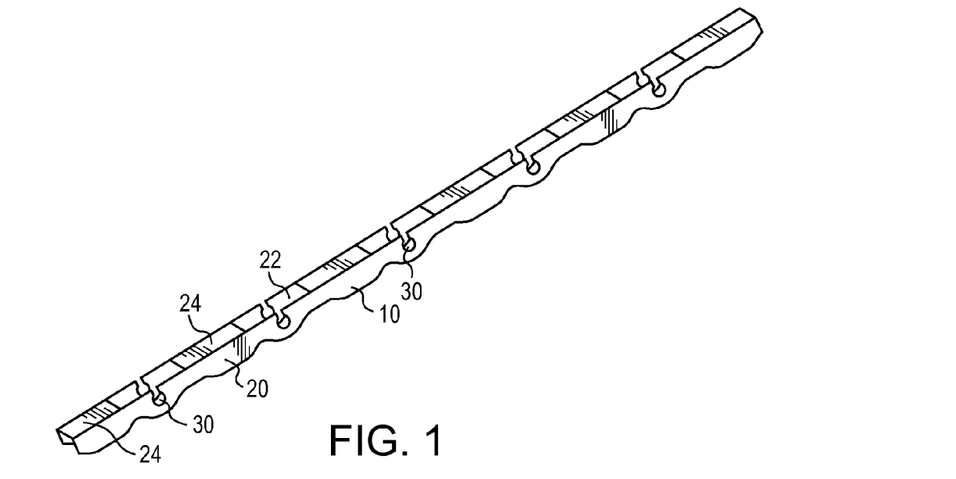
FIG. 1 is a top perspective view of a cryocane for pivotably supporting a plurality of cryovials.
Figure 2:
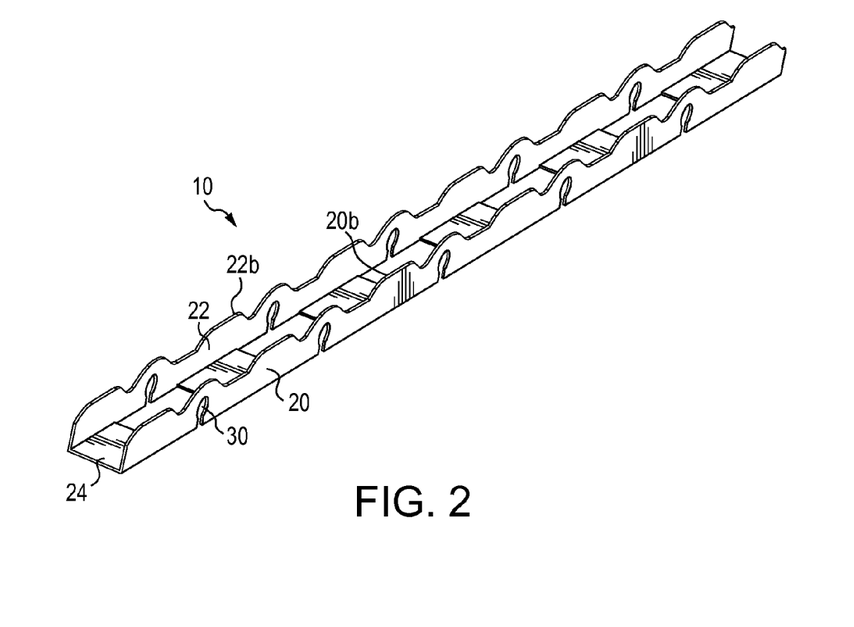
FIG. 2 is a bottom perspective view of the cryocane of FIG. 1.

With reference to FIGS. 1 and 6, the lower edges 20b, 22b of the respective first and second walls 20, 22 may be scalloped, or formed with an uneven profile along the length between the opposite ends of each wall 20, 22. The scalloped features are provided to provide a relatively wide part (shown with dimension T on FIG. 3) that is positioned to provide lateral support to a mid-portion 118 of a cryovial 100 disposed thereon (when the rod 10 is vertical), while other portions of the rod have relatively narrower heights (shown with dimension V on FIG. 3) that are aligned in positions near the points of engagement between the finger 112 and the recess 30, which may not require as much lateral support as further down upon the cryovial 100. This scalloped configuration removes excess material where it is not needed for weight and material cost concerns.

In some embodiments, the rod 10 may include a hook 40 on one or both of the opposite ends of the rod 10. The hook 40 may be an arcuate structure, like the hook on a conventional clothes hanger, while in other embodiments, the hook 40 may be formed with one or more straight members that extend from the rod at an angle to the longitudinal axis L (FIGS. 5, 6) of the rod 10. The hook 40 is configured to provide stable support for the rod 10 when the rod is aligned horizontally, where the hooks 40 interact with one or more edges of the bowl 200 (or other type of horizontal support structure) for filing or retrieving biological material with respect to the cryovial, or for vitrification. The one or more hooks 40 may also configured to allow the rod 10 to connect with a support cylinder 310 that in combination with the rod 10 is inserted vertically into the dewar 300 to provide support to the rod within the dewar 300. In other embodiments, the rod 10 may be formed without hooks 40 and the rod 10 fits within the support cylinder 320 by resting upon a mesh bottom of the support cylinder 320. In some embodiments, the hook 40 may be monolithically formed with the rod 10, while in other embodiments, the hook 40 may be fixed to the rod 10, or removably connected with the rod 10. In embodiments with other rods (cryocanes) discussed elsewhere herein, one or more hooks (similar to hooks 40) may be provided on one or both ends of those rods.

Figure 10:
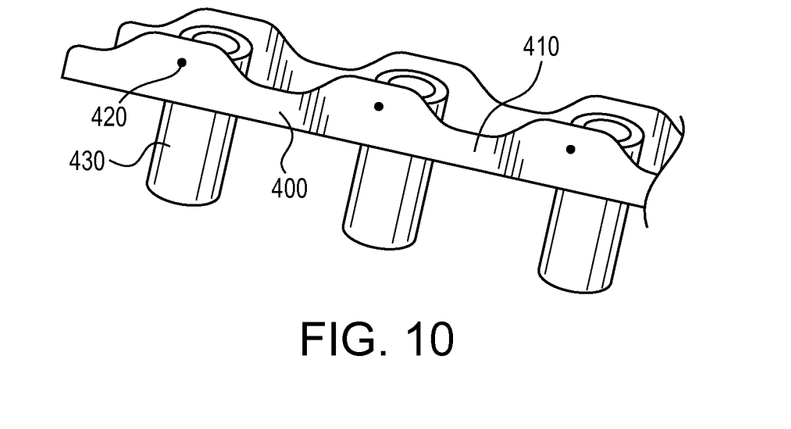
FIG. 10 is a perspective view of a portion of an alternate cryocane.
Figure 11:
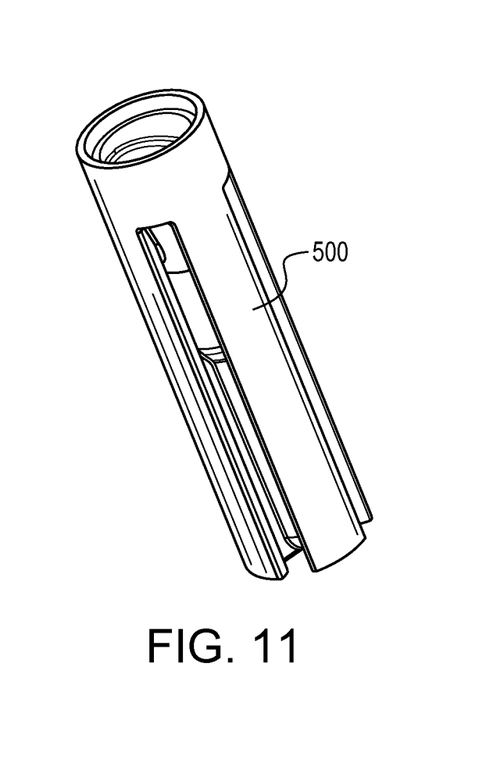
FIG. 11 is a perspective view of a cryovial configured for use with the cryocane of FIG. 10.

As shown in FIG. 10, another cryocane formed as a rod 410 is provided. The rod 410 is an elongate member that may pivotably support one or more cryocanes 500 (FIG. 11) in a vertical orientation when the rod is in a vertical orientation for storage in a dewar 300 (the orientation of FIG. 7) or in a horizontal orientation for placement or removal of biological matter or vitrification (the orientation of FIG. 5). The rod 410 pivotably supports one or more shells, or sleeves 430, which are each configured to receive a cryocane 500 within an internal volume 450 of the shell 430. The shells 430 are each pivotably mounted to the rod 410 with a pinned or other type of connection 420 to allow the shell 430 and cryovial 500 to pivot with respect to the rod 410, such that the cryovial 500 and shell 430 are maintained vertical in steady state regardless of the orientation of the rod 410. In some embodiments, the rod 410 may be formed from first and second walls (similar to first and second walls 20, 22, discussed above that each support one end of the pin 420 that supports the shell 430. The walls may be oriented to allow the cryovial 500 to fit therebetween when the rod 410 is in the vertical orientation for support of the cryovial 500 during long term storage within the dewar 300. In some embodiments, the shell 430 may be made from an insulating material, such as embodiments where the shell 430 is configured to receive the cryovial 500 after the vitrification process is complete. In other embodiments, the shell 430 may be made from a non-insulating material to allow for the vitrification process to occur with the cryovial 500 already disposed within the shell 430. In this embodiment, the cryovial 500 may be formed without fingers, as shown in FIG. 11.

While the preferred embodiments of the disclosed have been described, it should be understood that the invention is not so limited and modifications may be made without departing from the disclosure. The scope of the disclosure is defined by the appended claims, and all devices that come within the meaning of the claims, either literally or by equivalence, are intended to be embraced therein.

The invention claimed is:

1. A kit for performing long term storage of biological matter, comprising:

an elongate rod, extending between opposed first and second ends, and at least one holding point disposed upon the rod between the first and second ends, the holding point comprising a recess defined within a wall; and a cryovial with an internal volume configured to receive a biological sample therein, the cryovial comprising at least one finger that extends radially outward from an outer circumference thereof, wherein the finger is configured to releaseably mate with the at least one holding point upon the rod, wherein the at least one holding point is configured to receive and support the cryovial disposed upon the holding point in a range of orientations between a first orientation where the cryovial extends substantially parallel to a longitudinal axis of the rod to a second orientation where the cryovial extends substantially perpendicular to the longitudinal axis, wherein the cryovial is disposed in the first orientation when the rod is disposed such that the longitudinal axis of the rod is vertical, and the cryovial is disposed in the second orientation when the longitudinal axis of the rod is horizontal.

2. The kit of claim 1, wherein the at least one holding point is a plurality of holding points that are disposed between the first and second ends with spacings longer than a height of the cryovial.

3. The kit of claim 1, wherein the at least one holding point is a recess into a wall of the rod, wherein the recess comprises a neck portion and an inner cavity, wherein a width of the neck portion is greater than a width of the finger, and the width of the neck portion is smaller than a height of the finger.

4. The kit of claim 3, wherein the finger is rectangular in cross-section.

5. The kit of claim 1, wherein one or both of the first or second ends of the rod comprise hooks disposed thereon.

6. The kit of claim 1, wherein the cryovial is configured to hang vertically when mounted to the rod when the rod is in a vertical configuration and when the cryovial is in a horizontal configuration.

7. The kit of claim 1, wherein the rod comprises parallel first and second walls, with a spacing between the first and second walls slightly larger than a largest outer diameter of the cryovial.

8. The kit of claim 1, wherein the cryovial pivots from the first orientation to the second orientation when the rod is moved from the orientation where its longitudinal axis is vertical to the orientation where its longitudinal axis is horizontal.

9. The kit of claim 2, wherein each of the plurality of holding points are configured to simultaneously support a cryovial, wherein each cryovial supported by the rod simultaneously pivots from the first orientation to the second orientation when the rod is moved from the orientation where its longitudinal axis is vertical to the orientation where its longitudinal axis is horizontal.

10. The kit of claim 9, wherein each cryovial supported by the rod simultaneously pivots from the second orientation to the first orientation when the rod is moved from the orientation where its longitudinal axis is horizontal to the orientation where its longitudinal axis is vertical.

* * * * *